United States Patent [19]

Ohnuma et al.

[11] Patent Number: 5,081,234
[45] Date of Patent: Jan. 14, 1992

[54] 4'-DEMETHYLEPIPODOPHYLLOTOXIN GLYCOSIDES

[75] Inventors: Takeshi Ohnuma, Tokyo; Rika Obata, Kanagawa, both of Japan

[73] Assignee: Bristol-Myers Squibb Co., New York, N.Y.

[21] Appl. No.: 516,852

[22] Filed: Apr. 30, 1990

[51] Int. Cl.$^5$ .................. C07H 15/24; A61K 31/70
[52] U.S. Cl. .................. 536/17.1; 536/18.1; 536/18.2; 536/4.1
[58] Field of Search .................. 536/4.1, 18.1, 18.2, 536/17.1; 514/27, 35

[56] References Cited

U.S. PATENT DOCUMENTS

| | | | |
|---|---|---|---|
| 4,547,567 | 10/1985 | Umezawa et al. | 536/18.2 |
| 4,564,675 | 1/1986 | Kurabayashi et al. | 536/18.1 |
| 4,716,221 | 12/1987 | Umezawa et al. | 536/18.1 |
| 4,888,419 | 12/1989 | Saulnier et al. | 536/18.1 |
| 4,904,768 | 2/1990 | Saulnier et al. | 536/4.1 |
| 4,912,204 | 3/1990 | Ohnuma et al. | 536/18.1 |
| 4,916,217 | 4/1990 | Saulnier | 536/4.1 |
| 4,935,504 | 6/1990 | Saulnier et al. | 536/18.1 |
| 4,997,931 | 3/1991 | Ohnuma et al. | 536/17.1 |

FOREIGN PATENT DOCUMENTS 1-228999  9/1989  Japan .................. 536/18.1

OTHER PUBLICATIONS

J. Med. Chem., 1971, 14:936-940, Keller-Juslen et al.
Chem. Lett., 1987, 799-802, Saito et al.
Evelyn et al.; Carbohydrate Research 100:55-61 (1982).
Herzig et al.; Carbohydrate Research 153:162-167 (1986).

*Primary Examiner*—Johnnie R. Brown
*Assistant Examiner*—Nancy S. Carson
*Attorney, Agent, or Firm*—Mollie M. Yang

[57] ABSTRACT

The present invention relates to antitumor 4'-demethylepipodophyllotoxin glycosides having the formula

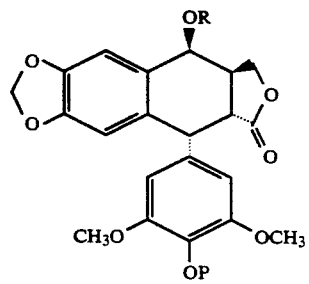

wherein R is a pentose selected from the group consisting of β-D-ribopyranosyl, peracyl β-D-ribopyranosyl, β-D-xylopyranosyl, peracyl β-D-xylopyranosyl, α-D-xylopyranosyl, peracyl α-D-xylopyranosyl, α-D-arabinopyranosyl, 3,4-O-($C_{1-4}$)alkylidene-D-ribopyranosyl, 2-O-acyl-3,4-O-($C_{1-4}$)alkylidene-D-ribopyranosyl, and β-D-ribofuranosyl; P is hydrogen, or —$PO_3H_2$ or a pharmaceutically acceptable salt thereof.

10 Claims, No Drawings

4'-DEMETHYLEPIPODOPHYLLOTOXIN GLYCOSIDES

BACKGROUND OF THE INVENTION

The present invention relates to novel antitumor compounds, their use in inhibiting tumor growth, and pharmaceutical compositions containing them. More particularly, the novel compounds are derivatives of 4'-demethylepipodophyllotoxin glycoside.

Etoposide and teniposide are two derivatives of 4'-demethylepipodophyllotoxin glucoside. The clinical efficacy of etoposide and teniposide in the treatment of a variety of cancers has been well documented and etoposide is currently approved in the United States for the treatment of small cell lung cancer and testicular cancer. The favorable therapeutic and pharmacological profiles of etoposide and teniposide have encouraged much activity in the search for other active analogs within the same class.

Most of the reported analogs and derivatives of etoposide and teniposide contain a D-glucose moiety, although derivatives having a different sugar are also known. Three D-galactopyranosides were reported in *J. Med. Chem.*, 1971, 10:936–40 and several L-glucopyranosides have been described in *Chem. Lett.*, 1987, 799–802. Our co-pending application U.S. Ser. No. 401,712, filed Sept. 1, 1989, discloses 4'-demethylepipodophyllotoxin altroside derivatives.

Further research effort by the present inventors in this area has led to the novel analogs disclosed and claimed herein. These new derivatives are distinguished over known 4'-demethylepipodophyllotoxins glycosides in having a pentose rather than a hexose. The novel compounds exhibit good activity against experimental leukemia in animal test models.

SUMMARY OF THE INVENTION

The present invention provides compounds of formula I:

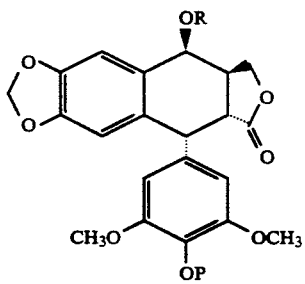

wherein R is a pentose selected from the group consisting of β-D-ribopyranosyl, peracyl β-D-ribopyranosyl, β-D-xylopyranosyl, peracyl β-D-xylopyranosyl, α-D-xylopyranosyl, peracyl α-D-xylopyranosyl, α-D-arabinopyranosyl, 3,4-O-($C_{1-4}$)alkylidene-D-ribopyranosyl, 2-O-acyl-3,4-O-($C_{1-4}$)alkylidene-D-ribopyranosyl, and β-D-ribofuranosyl; P is hydrogen, or $-PO_3H_2$ or a pharmaceutically acceptable salt thereof.

Also provided by the present invention are pharmaceutical compositions comprising a compound of formula I and a pharmaceutically acceptable carrier.

Another aspect of the present invention provides a method for inhibiting tumor growth in a mammalian host which comprises administering to said host an antitumor effective dose of a compound of formula I.

DETAILED DESCRIPTION OF THE INVENTION

As used herein in the specification and claims, unless otherwise indicated, the term "acyl" encompasses alkanoyl groups having one to five carbon atoms, benzoyl, phenylalkanoyl in which the carbon chain contains from one to five carbon atoms; "pharmaceutically acceptable salt" includes base salt with alkali metal, alkaline earth metal, ammonium, and tertiary amines such as triethylamine, trimethylamine, pyridine and the like; "alkylidene" includes straight and branched carbon chains.

A preferred embodiment of the present invention provides compounds of formula I wherein the sugar moiety R is selected from β-D-ribopyranosyl, peracyl β-D-ribopyranosyl, 3,4-O-($C_{1-4}$)alkylidene-D-ribopyranosyl, and 2-O-acyl-3,4-O-($C_{1-4}$)alkylidene-D-ribopyranosyl.

Another preferred embodiment of the present invention provides compounds of formula I wherein the sugar moiety R is selected from β-D-xylopyranosyl and α-D-xylopyranosyl.

Another preferred embodiment of the present invention provides compounds of formula I wherein P is hydrogen.

A more preferred embodiment of the present invention provides compounds of formula I wherein R is selected from the group consisting of β-D-ribopyranosyl, peracetyl β-D-ribopyranosyl, β-D-xylopyranosyl, α-D-xylopyranosyl, and 3,4-O-($C_{1-4}$)alkylidene-D-ribopyranosyl.

The 4'-demethylepipodophyllotoxin glycosides of the present invention are prepared by condensing 4'-protected 4'-demethylepipodophyllotoxin with an appropriately protected sugar. 4'-Protected 4'-demethylepipodophyllotoxins are known in the art; for example, 4'-carbobenzyloxy-4'-demethylepipodophyllotoxin and its preparation are described in U.S. Pat. No. 3,524,844. (Carbobenzyloxy is hereinafter referred to as CBZ.) The choice of the phenol protecting group is not critical and may include the formation of acyl derivatives such as esters or carbonates, ethers, acetals, and the like in accordance with conventional methods well-known in the art.

The sugar starting materials are either commercially available or they may be readily prepared by following literature procedures. Thus, for example, 2,3,4-O-triacetyl xylopyranose may be prepared by the method described in Herzig and Nudelman, *Carbohydrate Res.*, 1986, 153:162–7; peracetyl arabinopyranose may be prepared according to the method described in Evelyn and Hall, *Carbohydrate Res.*, 1982, 100:55–61 and then selectively deacetylated using the Herzig method, supra; and peracetyl-D-ribose may be prepared according to the method described by H. Zinner, *Chem. Ber.*, 1950, 83:153–6. Again, the choice of protecting groups for the sugar hydroxy groups is not particularly restricted and may be include other acyl groups such as formyl, acetyl, propionyl and benzoyl. A mixture of the α- and β-anomers or the individual anomers may be used as the sugar starting material.

The condensation between the sugar and the aglycone is carried out in a reaction inert organic solvent, for example methylene or ethylene chloride at a temperature below 0° C., e.g., from about −10° to −25° C., and in the presence of a catalyst such as boron trifluoride ethyl etherate. The sugar reactant and boron trifluoride ethyl etherate are used in at least equimolar amount relative to the aglycone; but preferably they are used in excess of from about 1.5 to about 5 equivalents relative to the aglycone. The reaction time may be from minutes to about 2 hours depending on the nature of the reactants. The action of boron trifluoride ethyl etherate may be quenched by the addition to the reaction mixture a tertiary amine such as pyridine or triethylamine.

The condensation product may be a mixture of α- and β-glycosides in which case the mixture may be separated into the two anomers and each is then deprotected, or the mixture of anomers may be deprotected first, followed by separation of the deprotected products; the order is not critical. Separation of anomers may be effected by conventional techniques such as column chromatography. The sugar hydroxy protecting groups and the phenol protecting group may be chosen such that they may be removed in one step or stepwise. The deprotection may be effected using conventional deblocking methods, the choice of which depends on the nature of the protecting group employed. Typical methods that may be mentioned include hydrogenation, acid or base catalyzed hydrolysis, and alcoholysis in the presence of a metal catalyst such as zinc powder or zinc acetate.

Where the sugar hydroxy groups are protected with an acyl group, selective removal of the phenol protecting group provides compounds of formula I wherein P is hydrogen and R is a peracylated sugar. Removal of the hydroxy protecting acyl group provides compounds of formula I wherein P is hydrogen and R is a deacylated pentose. Compounds of formula I wherein P is hydrogen and R is 3,4-O-alkylidene-D-ribopyranose are obtained by reacting the ribopyranoside with an aldehyde or ketone having one to four carbon atoms, or a lower acetal or ketal thereof. The reaction is carried out at room temperature in a reaction inert solvent such as methylene or etheylene chloride, or chlorform, and in the presence of an acid such as a sulfonic acid such as p-toluenesulfonic acid.

Compounds of formula I wherein P is hydrogen thus obtained may be further derivatized to provide the corresponding 4'-phosphate (compounds of formula I wherein P is $-PO_3H_2$). This may be accomplished by using known methods for converting a hydroxy group into its phosphate ester. Such methods include reacting a compound of formula I wherein P is hydrogen with a phosphorylating agent such as phosphorous oxychloride followed by hydrolysis to afford the phosphate product; or reacting the former with diphenyl chlorophosphate followed by catalytic hydrogenation to generate the phosphate ester. Pharmaceutically acceptable salts may be obtained by treating the acid with a base such as an alkali metal carbonate, bicarbonate or hydroxide.

BIOLOGICAL ACTIVITY

Representative pentose derivatives of etoposide were comparatively tested with the parent compound for in vitro cytotoxicity and in vivo antitumor activity in mice.

In Vitro Cytotoxicity

Murine melanoma B16-F10 cells were grown and maintained at 37° C. under a humidified atmosphere in a 5% $CO_2$ incubator in Eagle's MEM medium (Nissui) containing kanamycin (60 μg/ml), and supplemented with heat inactivated fetal calf serum (10%) and nonessential amino acids (0.6%). For in vitro cytotoxicity experiments, exponentially growing B16-F10 cells were harvested, counted, and suspended in the culture medium at the concentration of $2.0 \times 10^4$ cells/ml. Twenty-four hours after planting cell suspension (180 μl) into wells of a 96-well microtiter plate, test materials (20 μl) were added to the wells and the plates were incubated for 72 hours. The cytotoxic activity against B16-F10 cells was colorimetrically determined at 540 nm after staining viable cells with neutral red solution.

In Vivo Antitumor Activity

Representative compounds of the present invention were evaluated against murine P388 lymphocytic leukemia. Female $CDF_1$ mice were inoculated with $1.0 \times 10^6$ of leukemia cells intraperitoneally (day 0), and test materials were intraperitoneally administered to mice once on day 1 (Q1D×1). Treated animals were observed for 45 days. The median survival time (MST) of each group was recorded, and antitumor activity was expressed as T/C % values calculated by the following equation:

$$T/C\% = (MST \text{ of treated} \div MST \text{ of control}) \times 100$$

Compounds having a T/C % value of over 125% are considered to have significant antitumor activity. For the in vivo evaluation, only the maximum % T/C is listed, along with the dose that resulted in the maximum % T/C.

The in vitro and in vivo results are summarized in Table 1.

TABLE 1

| | In Vitro Cytotoxicity and In Vivo Antitumor Activity | | |
|---|---|---|---|
| | Cytotoxicity vs B16-F10 | Antitumor Activity vs P388 | |
| Compound | $IC_{50}$, μg/ml | Dose (mg/kg) | Max % T/C |
| Compound D | 18.0 | 30 | 130 |
| Compound E | 4.0 | 120 | 171 |
| Compound F | 1.0 | 60 | 181 |
| Compound G | 2.5 | 120 | 152 |
| Compound H | 0.53 | 30 | 150 |
| Compound I | 2.3 | 10 | 140 |
| Compound K | 28.0 | 10 | 125 |
| Etoposide | 0.21 | 120 | 188 |

The test results indicate that compounds of the present invention are useful as antitumor compounds. Accordingly, the present invention provides a method for inhibiting mammalian tumors which comprises administering an effective tumor-inhibiting dose of an antitumor compound of formula I to a tumor bearing host. For this purpose, the drug may be administered by conventional routes including, but not limited to, intravenous, intramuscular, intratumoral, intraarterial, intralymphatic, and oral; intravenous administration is preferred.

A further aspect of the present invention provides a pharmaceutical composition which comprises a compound of formula I and a pharmaceutically acceptable carrier. The antitumor composition may be made up of any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

Optimal dosages and regimens for a given mammalian host can be readily ascertained by those skilled in the art. It will, of course, be appreciated that the actual dose used will vary according to the particular composition formulated, the particular compound used, the mode of application and the particular site, host and disease being treated. Many factors that modify the action of the drug will be taken into account including age, weight, sex, diet, time of administration, route of administration, rate of excretion, condition of the patient, drug combinations, reaction sensitivities and severity of the disease.

The following examples are only meant to illustrate the invention and are not to be construed as in any way limiting the scope of the invention which is defined solely by the claims appended to the specification.

EXAMPLE 1

Preparation of 4'-O-CBZ-4'-demethyl-4-O-(2,3,5-tri-O-acetyl-$\beta$-D-ribofuranosyl)epipodophyllotoxin (Compound A) and 4'-O-CBZ-4'-demethyl-4-O-(2,3,4-tri-O-acetyl-$\beta$-D-ribopyranosyl)epipodophyllotoxin (Compound B)

To a stirred solution of peracetyl-D-ribose (prepared according to the procedure described in Zinner, *Chem. Ber.*, 1950, 83:153–6) (1.8 g, 5.66 mmol) in methanol (40 ml) was added alumina (Woelm-N-super I, 18 g), and the suspension was refluxed for 8 hrs. The reaction mixture was cooled to room temperature, and the inorganic substance was filtered off and washed with dichloromethane. The combined filtrates were concentrated in vacuo to give a mixture of 2,3,5-tri-O-acetyl-D-ribofuranose and 2,3,4-tri-O-acetyl-O-ribopyranose (1.24 g, 79%) as pale yellow oil which, without purification, was subjected to the following glycosidation.

To a cooled ($-15°$ to $-20°$ C.) solution of methanol-solvated 4'-O-CBZ-4'-demethylepipodophyllotoxin (470 mg, 0.83 mmol, dried at 120° C. in vacuo prior to use) and the above tri-O-acetyl-D-ribose (360 mg, 1.3 mmol) in dichloroethane (40 ml) was added $BF_3 \cdot Et_2O$ (370 $\mu$l, 3 mmol) under argon, and the mixture was stirred at $-15°$ to $-20°$ C. for 1 hr. After addition of triethylamine (0.5 ml), the mixture was washed with water and dried over anhyd. $Na_2SO_4$. The organic solvent was evaporated in vacuo, and the resulting crude residue (966 mg) was separated by a silica gel column ($CH_2Cl_2$/MeOH=100/1) to give Compound A (138 mg, 21%), Compound B (264 mg, 40%), and a mixture of Compounds A and B (144 mg, 22%).

Compound A

UV $\lambda_{max}$ (MeOH) nm ($\epsilon$) 292 (4,300).

$^1$H NMR (CDCl$_3$) $\delta$ 7.4 (5H, m, PhCH$_2$OCO), 5.27 (1H, m, 3''-H)*, 5.25 (2H, s, PhCH$_2$OCO), 5.21 (1H, s like, 1''-H), 5.19 (1H, d like, J=7 Hz, 2''-H), 4.36 (1H, m, 4''-H), 4.27 (1H, m, 5''-H), 4.15 (1H, dd, J=5.5 & 11.9 Hz, 5''-H), 2.11, 2.10, 2.07 (3H×3, s×3, OAc×3).

*As used herein, the number before the quotation mark ('') refers to the position on the sugar moiety.

Anal. Calcd. for C$_{40}$H$_{40}$O$_{17}$: C 60.60, H 5.09. Found: C 60.55, H 5.09.

Compound B

IR $\nu_{max}$ (KBr) cm$^{-1}$ 3500 (br.), 1770, 1750, 1600.

UV $\lambda_{max}$ (MeOH) nm ($\epsilon$) 292 (3,900).

$^1$H NMR (CDCl$_3$) $\delta$ 7.4 (5H, m, PhCH$_2$OCO), 5.39 (1H, t, J=3.3 Hz, 3''-H), 5.25 (2H, s, PhCH$_2$OCO), 5.16 (1H, m, 4''-H), 5.00 (1H, d, J=4.4 Hz, 1''-H), 4.97 (1H, m, 2''-H), 3.92 (1H, m, 5''-H), 3.77 (1H, d, J=5.9 Hz, 5''-H), 2.11, 2.09, 2.03 (3H×3, s×3, OAc×3).

Anal Calcd. for C$_{40}$H$_{40}$O$_{17}$: C 60.60, H 5.09. Found: C 60.38, H 5.11.

EXAMPLE 2

4'-Demethyl-4-O-($\beta$-D-ribofuranosyl)epipodophyllotoxin (Compound D)

A. Preparation of 4'-Demethyl-4-O-(2,3,5-tri-O-acetyl-$\beta$-D-ribofuranosyl)epipodophyllotoxin (Compound C).

A stirring solution of Compound A (135 mg, 0.17 mmol) in ethanol-acetone (4:1, 25 ml) was hydrogenated for 2.5 hrs in the presence of 10% palladium on carbon (135 mg) at 1 atm. The catalyst was then filtered off and the filtrate concentrated to give the title compound (129 mg, ca. 100%) as an oil, which was crystallized from ethanol to afford 58 mg of the title compound as colorless crystals, m.p. 123°–125° C., estimated purity 80% by HPLC.

Compound C

IR $\nu_{max}$ (KBr) cm$^{-1}$ 3400 (br.), 1750, 1610.

UV $\lambda_{max}$ (MeOH) nm ($\epsilon$) 240 (sh, 12,300), 285 (4,040).

$^1$H NMR (CDCl$_3$) $\delta$ 5.27 (1H, dd, J=4.8, 7.3 Hz, 3''-H), 5.21 (1H, s like, 1''-H), 5.20 (1H, d like, J=4.8 Hz, 2''-H), 4.36 (1H, m, 4''-H), 4.26 (2H, m, 5''-H).

FAB-MS m/z 658 (M+).

B. Preparation of 4'-Demethyl-4-O-($\beta$-D-ribofuranosyl)epipodophyllotoxin (Compound D).

To a solution of Compound C (40 mg, 0.06 mmol) in methanol (10 ml) was added zinc acetate dihydrate (40 mg), and the mixture was refluxed overnight. After evaporation of the solvent, the residue, diluted with CH$_2$Cl$_2$/i-PrOH/AcOH (8:1:0.1), was washed with water and dried over anhyd. Na$_2$SO$_4$. The organic solvent was concentrated in vacuo to give the crude residue, which was purified by a silica gel column (CH$_2$Cl$_2$/MeOH=10/1) to obtain the title compound (19 mg, 59%) as a colorless oil, m.p. 253°–255° C., estimated purity 95% by HPLC.

IR $\nu_{max}$ (KBr) cm$^{-1}$ 3400 (br.), 1760, 1610.

UV $\lambda_{max}$ (MeOH) nm ($\epsilon$) 240 (sh, 11,200), 284 (3,750).

$^1$H NMR (DMSO-d$_6$) $\delta$ 5.06 (1H, d, J=4.4 Hz, D$_2$O exch., 2''-OH), 4.98 (1H, s like, 1''-H), 4.81 (1H, d, J=6.6 Hz, D$_2$O exch., 3''-OH), 4.73 (1H, t, J=5.7 Hz, D$_2$O exch., 5''-OH), 3.94 (1H, m, 3''-H), 3.82 (1H, m, 4''-H), 3.71 (1H, t like, J=5 Hz), 3.59 (1H, m, 5''-H), 3.42 (1H, dt, J=6.0 & 11.9 Hz, 5''-H).

FAB-MS m/z 532 (M+), 555 (M+Na)+.

EXAMPLE 3

4'-Demethyl-4-O-(2,3,4-tri-O-acetyl-$\beta$-D-ribopyranosyl)epipodophyllotoxin (Compound E)

According to the procedure of Example 2, part A, 350 mg (0.44 mmol) of Compound B was hydrogenated to give the title compound (306 mg, ca. 100%) as colorless solid, which was crystallized from ethanol to obtain colorless crystal, m.p. 150°–153° C., estimated purity 95% by HPLC.

IR $\nu_{max}$ (KBr) cm$^{-1}$ 3400 (br.), 1760, 1610.
UV $\lambda_{max}$ (MeOH) nm ($\epsilon$) 240 (sh, 12,600), 285 (4,100).
$^1$H NMR (CDCl$_3$) $\delta$ 5.40 (1H, m, 3″-H), 5.16 (1H, m, 4″-H), 5.01 (1H, d, J=4.4 Hz, 1″-H), 4.97 (1H, t, J=3.7 Hz, 2″-H), 3.92 (2H, m, 5″-H).
FAB-MS m/z 658 (M+).
Anal. Calcd. for C$_{32}$H$_{34}$O$_{15}$: C 58.36, H 5.20. Found: C 58.02, H 5.19.

EXAMPLE 4

4′-Demethyl-4-O-($\beta$-D-ribopyranosyl)epipodophyllotoxin (Compound F)

According to the procedure of Example 2, part B, 60 mg (0.09 mmol) of Compound E was deacetylated to give the title compound (30 mg, 62%) as a colorless solid, m.p. 246°–248° C., estimated purity 90% by HPLC.
IR $\nu_{max}$ (KBr) cm$^{-1}$ 3460 (br.), 1760, 1610.
UV $\lambda_{max}$ (MeOH) nm ($\epsilon$) 240 (sh, 11,200), 285 (3,750).
$^1$H NMR (DMSO-d$_6$) $\delta$ 4.95 (1H, d, J=6.2 Hz, D$_2$O exch., 2″-OH), 4.77 (1H, d, J=6.6 Hz, D$_2$O exch., 4″-OH), 4.75 (1H, d, J=4.8 Hz, D$_2$O exch., 3″-OH), 4.71 (1H, d, J=5.5 Hz, 1″-H), 3.74 (1H, dd, J=2.3 & 4.6 Hz, 3″-H), 3.58 (2H, m, 4″- and 5″-H), 3.27 (2H, m, 2″- and 5″-H).
FAB-MS m/z 532 (M+), 555 (M+Na)+.
Anal. Calcd. for C$_{26}$H$_{28}$O$_{12}$: C 58.64, H 5.30. Found: C 58.55, H 6.16.

EXAMPLE 5

4′-Demethyl-4-O-(3,4-O-ethylidene-$\beta$-D-ribopyranosyl)epipodophyllotoxin (Compound G)

To a stirred suspension of Compound F (90 mg, 0.17 mmol) in dichloromethane (4 ml) was added acetaldehyde (20 $\mu$l, 0.35 mmol) and p-toluenesulfonic acid (7 mg) and stirred at room temperature overnight. The mixture was washed with water and dried over anhyd. Na$_2$SO$_4$. The solvent was concentrated in vacuo, and the resulting crude residue (101 mg) was purified by silica gel column (CH$_2$Cl$_2$/MeOH=20/1) to give 33 mg (35%) of the title compound as colorless crystals from methanol, m.p. 246°–249° C., estimated purity 85% by HPLC.
IR $\nu_{max}$ (KBr) cm$^{-1}$ 1760, 1610.
UV $\lambda_{max}$ (MeOH) nm ($\epsilon$) 238 (sh, 12,000), 286 (3,770).
$^1$H NMR (CDCl$_3$) $\delta$ 5.14 (1H, q, J=4.8 Hz, 6″-H), 5.08 (1H, d, J=5.9 Hz, 1″-H), 4.41 (1H, dd, J=4.0 & 7.0 Hz, 3″-H), 4.22 (1H, dt, J=3.3 & 7.0 Hz, 4″-H), 3.80 (1H, dd, J=3.3 & 12.8 Hz, 5″-H), 3.75 (1H, dd, J=3.3 & 12.8 Hz, 5″-H), 3.68 (1H, dt, J=4.0 & 5.9 Hz, 2″-H), 2.30 (1H, d, J=5.9 Hz, D$_2$O exch., 2″-OH), 1.50 (3H, d, J=4.8 Hz, 7″-Me).
FAB-MS m/z 558 (M+).
Anal. Calcd. for C$_{28}$H$_{30}$O$_{12}$.½H$_2$O: C 59.26, H 5.51. Found: C 59.34, H 5.35.

EXAMPLE 6

4′-Demethyl-4-O-($\beta$-D-xylopyranosyl)epipodophyllotoxin (Compound H) and
4′-Demethyl-4-O-($\alpha$-D-xylopyranosyl)epipodophyllotoxin (Compound I)

A. Preparation of 4′-O-CBZ-4′-demethyl-4-O-(2,3,4-tri-O-acetyl-$\beta$-D-xylopyranosyl)epipodophyllotoxin and its 1″-$\alpha$-anomer.

To a cooled (−15° to −20° C.) solution of 2,3,4-tri-O-acetylxylopyranose (prepared according to the procedure of Heizig, Carbohydrate Res., 1986, 153:162–7) (490 mg, 1.78 mmol) and 4′-demethyl-4′-CBZ-epipodophyllotoxin (534 mg, 1.0 mmol) in dry 1,2-dichloroethane (40 ml) was added BF$_3$-Et$_2$O (0.50 ml, 4.0 mmol), and the mixture was stirred at the same temperature for 30 min. After addition of pyridine (0.4 ml), the mixture was washed with 5% HCl and water and dried over anhyd. Na$_2$SO$_4$. After removal of the solvent, the residue was chromatographed on a silica gel column (1% MeOH - CH$_2$Cl$_2$) to give 631 mg (80%) of an inseparable mixture of $\alpha$- and $\beta$-anomers of the title compound.
IR $\nu_{max}$ (KBr) cm$^{-1}$ 1730–1770 (broad), 1600.
$^1$H NMR (CDCl$_3$) $\delta$ 2.03, 2.10, and 2.13 (3H$\times$3, each s, COCH$_3$$\times$3), 3.07 (6H, s, OCH$_3$$\times$2), 5.15 and 5.40 (2H, each d, J=12 Hz, CH$_2$C$_6$H$_5$), 5.98 (2H, s, OCH$_2$O), 6.28 (2H, s, 2′,6′-H), 6.54 (1H, s, 6-H), 6.79 (1H, s, 5-H), 7.36 (5H, s, CH$_2$C$_6$H$_5$).

B. Preparation of 4′-Demethyl-4-O-($\beta$-D-xylopyranosyl)epipodophyllotoxin (Compound H) and 4′-Demethyl-4-O-($\alpha$-D-xylopyranosyl)epipodophyllotoxin (Compound I).

A mixture of the $\alpha$- and $\beta$-anomers as prepared in part A above (600 mg, 0.75 mmol) and zinc acetate dihydrate (880 mg, 4 mmol) in MeOH (30 ml) was refluxed for 10 hrs with stirring, and the mixture was evaporated to dryness. The residue, diluted with CH$_2$Cl$_2$ (30 ml) and acetic acid (0.5 ml), was washed with water and aq. NaHCO$_3$ and dried over anhyd. Na$_2$SO$_4$. After removal of the solvent, the residue was chromatographed on a silica gel column (10% MeOH-CH$_2$Cl$_2$) to give 261 mg (52%) of the triol as a mixture of $\alpha$- and $\beta$-anomers. This triol (86 mg, 0.13 mmol) in ethyl acetate (10 ml) was hydrogenated over 10% palladium on carbon (20 mg) under one atmospheric pressure. The catalyst was removed by filtration and washed with acetone. The filtrate and washings were evaporated to dryness, and the residue was chromatographed on a silica gel column (10% MeOH-CH$_2$Cl$_2$) to give 28 mg (39%) of Compound H and 24 mg (34%) of Compound I.

Compound H

MP 244°–247° C.
IR $\nu_{max}$ (KBr) cm$^{-1}$ 3400, 1760, 1610.
UV $\lambda_{max}$ (MeOH) nm ($\epsilon$) 240 (sh, 11,420), 285 (3,700).
$^1$H NMR (DMSO-d$_6$) $\delta$ 4.98 (1H, d, J=4.8 Hz, 2″-OH), 4.97 (1H, d, J=5.2 Hz, 4″-OH), 4.95 (1H, d, J=4.8 Hz, 3″-OH), 4.38 (1H, d, J=7.3 Hz, 1″-H), 3.75 (1H, dd, J=5.4 & 11.1 Hz, 5″-Heq), 3.28 (1H, m, 4″-H), 3.1 (2H, m, 3″,5″-Hax), 2.98 (1H, m, 2″-H).
FAB-MS m/z 532 (M+).

Compound I

MP 260°–263° C.
IR $\nu_{max}$ (KBr) cm$^{-1}$ 3400, 1760, 1610.
UV $\lambda_{max}$ (MeOH) nm ($\epsilon$) 240 (sh, 10,100), 285 (3,300).
$^1$H NMR (DMSO-d$_6$) $\delta$ 5.01 (1H, d, J=7.7 Hz, 2″-OH), 4.87 (1H, d, J=4.8 Hz, 4″-OH), 4.82 (1H, d, J=4.2 Hz, 1″-H), 4.78 (1H, d, J=4.0 Hz, 3″-OH), 3.43 (1H, m, 5″-H), 3.1–3.3 (4H, m, 2″,3″,4″,5″-H).
FAB-MS m/z 532 (M+), 555 (M+Na)+.

EXAMPLE 7

4′-Demethyl-4-O-($\alpha$-D-arabinopyranosyl)epipodophyllotoxin (Compound K)

A. Preparation of 4′-O-Carbobenzyloxy-4′-demethyl-4-O-(2,3,4-tri-O-acetyl-D-arabionopyranosyl)epipodophyllotoxin (Compound J).

A suspension of peracetyl-D-arabinose (prepared according to the method of Evelyn, *Carbohydrate Res.*, 1982, 100:55–61) (3 g, 9.4 mmol) and alumina (50 mg) in methanol (200 ml) was refluxed for 5 hrs. After filtration of the inorganic substance, the filtrate was concentrated in vacuo to give 2,3,4-tri-O-acetyl-D-arabinopyranose (1.46 g, 56%) as an oil.

$^1$H NMR (60 MHz, CDCl$_3$) δ 4.9–5.5 (3H, m), 3.7–4.4 (3H, m), 3.40 (1H, s, D$_2$O exch., 1-OH), 2.1 (9H, s, 3×OAc).

To a cooled (−14° C.) solution of 4'-demethyl-4'-CBZ-epipodophyllotoxin (567 mg, 1 mmol) and the above triacetylarabinose (360 mg, 1.3 mmol) in dichloroethane (40 ml) was added BF$_3$.Et$_2$O (370 μl, 3 mmol), and the reaction mixture was stirred at −14° C. for 1 hr. The reaction was quenched with triethylamine (0.5 ml), and the mixture was washed with water and dried over anhyd. Na$_2$SO$_4$. The organic solvent was evaporated to give an oil (974 mg), which was chromatographed on a silica gel column (CH$_2$Cl$_2$/MeOH=50/1) to obtain 252 mg (31%) of Compound J as a colorless powder.

$^1$H NMR (80 MHz, CDCl$_3$) δ 7.2–7.5 (5H, m, PhCH$_2$OCO), 7.00 (1H, s, 5-H), 6.47 (1H, s, 8-H), 6.26 (2H, s, 2',6'-H), 5.96 (2H, s, OCH$_2$O), 5.25 (2H, s, PhCH$_2$OCO), 5.12 (1H, d, J=3 Hz, 4-H), 3.9–5.1 (9H, m) 3.68 (6H s, 3',5'-OMe), 3.3 (1H, m, 2-H), 2.90 (1H, m, 3-H), 2.14, 2.06, and 2.00 (3H×3, each s, 3×OAc).

FAB-MS m/z 793 (M+1)$^+$.

B. Preparation of 4'-Demethyl-4-O-(α-D-arabinopyranosyl)epipodophyllotoxin (Compound K)

A suspension of Compound J (250 mg, 0.3 mmol) and zinc acetate (50 mg) in methanol (20 ml) was refluxed with stirring for 2 hrs. The reaction mixture was concentrated in vacuo to give the deacetyl product as crude solid which, without purification, was submitted to the following hydrogenolysis.

A stirring solution of the above crude solid in ethanol-acetone (4:1, 10 ml) was hydrogenated overnight in the presence of 10% Pd-C (200 mg) at 1 atm. Then the catalyst was filtered off, and the filtrate was concentrated in vacuo to give the crude solid (245 mg), which was chromatographed on a silica gel column (CH$_2$Cl$_2$/MeOH=20/1) to obtain 88 mg (55%) of the title compound, m.p. 258°–260° C., estimated purity 95% by HPLC.

IR ν$_{max}$ (KBr) cm$^{-1}$ 3400 (br.), 1760, 1610.

UV λ$_{max}$ (MeOH) nm (ε) 238 (sh, 13,200), 285 (4,300).

$^1$H NMR (DMSO-d$^6$) δ 5.19 (1H, d, J=3.9 Hz, D$_2$O exch., 2"-OH), 4.72 (1H, d, J=5.1 Hz, D$_2$O exch., 3"-OH), 4.56 (1H, d, J=3.8 Hz, D$_2$O exch., 4"-OH), 4.12 (1H, d, J=6.8 Hz, 1"-H), 3.82 (1H, dd, J=2.5 & 12.0 Hz, 5"-H), 3.64 (1H, br.s, 4"-H), 3.50 (1H, d like, J=12.0 Hz, 5"-H), 3.33 (2H, m, 2",3"-H).

FAB-MS m/z 532 (M+).

What is claimed is:

1. A compound having the formula

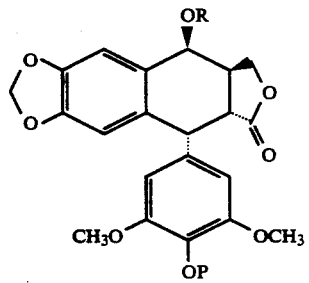

wherein

R is a pentose selected from the group consisting of β-D-ribopyranosyl, peracyl β-D-ribopyranosyl, β-D-xylopyranosyl, peracyl β-D-xylopyranosyl, α-D-xylopyranosyl, peracyl α-D-xylopyranosyl, α-D-arabinopyranosyl, 3,4-O-(C$_{1-4}$)alkylidene-D-ribopyranosyl, 2-O-acyl-3,4-O-(C$_{1-4}$)alkylidene-D-ribopyranosyl, and β-D-ribofuranosyl;

P is hydrogen or —PO$_3$H$_2$ or a pharmaceutically acceptable salt thereof.

2. A compound of claim 1 wherein R is selected from the group consisting of β-D-ribopyranosyl, peracyl β-D-ribopyranosyl, 3,4-O-(C$_{1-4}$)alkylidene-D-ribopyranosyl, and 2-O-acyl-3,4-O-(C$_{1-4}$)alkylidene-D-ribopyranosyl.

3. A compound of claim 1 wherein R is selected from β-D-xylopyranosyl and α-D-xylopyranosyl.

4. A compound of claim 1 which is 4'-demethyl-4-O-(β-D-ribofuranosyl)epipodophyllotoxin.

5. A compound of claim 1 which is 4'-demethyl-4-O-(2,3,4-tri-O-acetyl-β-D-ribopyranosyl)epipodophyllotoxin.

6. A compound of claim 1 which is 4'-demethyl-4-O-(β-D-ribopyranosyl)epipodophyllotoxin.

7. A compound of claim 1 which is 4'-demethyl-4-O-(3,4-O-ethylidene-β-D-ribopyranosyl)epipodophyllotoxin.

8. A compound of claim 1 which is 4'-demethyl-4-O-(β-D-xylopyranosyl)epipodophyllotoxin.

9. A compound of claim 1 which is 4'-demethyl-4-O-(α-D-xylopyranosyl)epipodophyllotoxin.

10. A compound of claim 1 which is 4'-demethyl-4-O-(α-D-arabinopyranosyl)epipodophyllotoxin.

* * * * *